(12) United States Patent
Kamikawa et al.

(10) Patent No.: US 6,723,870 B2
(45) Date of Patent: Apr. 20, 2004

(54) METHOD FOR PRODUCING ANTHRACENES

(75) Inventors: Takashi Kamikawa, Nara (JP); Junji Morimoto, San Marino, CA (US)

(73) Assignee: Sumitomo Chemical Company, Limited, Osaka (JP)

( * ) Notice: Subject to any disclaimer, the term of this patent is extended or adjusted under 35 U.S.C. 154(b) by 22 days.

(21) Appl. No.: 10/252,553

(22) Filed: Sep. 24, 2002

(65) Prior Publication Data

US 2003/0069443 A1 Apr. 10, 2003

(30) Foreign Application Priority Data

Sep. 27, 2001 (JP) .......................................... 2001-297064

(51) Int. Cl.[7] .................. C07C 69/76; C07C 209/78; C07C 41/18; C07C 39/12; C07C 1/20
(52) U.S. Cl. .................. 560/80; 564/427; 568/633; 568/733; 585/469; 585/457
(58) Field of Search .................. 560/80; 564/427; 568/633, 733; 585/469, 457

(56) References Cited

U.S. PATENT DOCUMENTS 4,463,162 A * 7/1984 Nogami et al. ............. 528/190
5,501,821 A * 3/1996 Willand et al. ............. 252/582

OTHER PUBLICATIONS

M.A. Tius et al., "A Bifunctional Anthraquinone Synthon", Tetrahedron Letters, vol. 29, No. 52, (1998), pp. 6909–6912.
T. Brotin et al., "A Novel Small Molecular Luminescent Gelling Agent for Alcohols", J. Chem. Soc., Chem. Communication, (1991), pp. 416–418.

* cited by examiner

Primary Examiner—Peter O'Sullivan
(74) Attorney, Agent, or Firm—Sughrue Mion, PLLC

(57) ABSTRACT

Disclosed is a method for producing anthracene of formula (II) below by mixing a reaction mixture with a primary alcohol, wherein the reaction mixture is a reaction mixture obtained by reacting a metal hydride with an anthraquinone of formula (I):

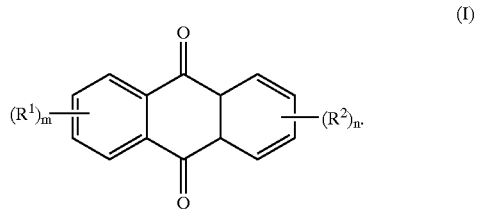

(I)

9 Claims, No Drawings

METHOD FOR PRODUCING ANTHRACENES

FIELD OF THE INVENTION

The present invention relates to a method for producing anthracenes.

BACKGROUND OF THE INVENTION

Anthracenes are useful production intermediates for preparing dyes, etc., and there has been known a method for producing the compound by reacting an anthraquinone with a metal hydride (*Tetrahedron Lett.*, Vol. 29, No. 52, page 699 (1988), *J. Chem. Soc. Chem. Commun.*, page 416 (1991)).

The conventional method, however, could not necessarily provide anthracenes in a good yield.

SUMMARY OF THE INVENTION

According to the present invention, an anthracene compound can be produced in a good yield.

The present invention provides:

a method for producing an anthracene of formula (II)

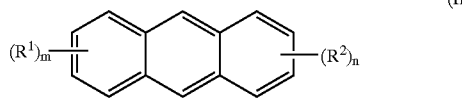

(II)

wherein $R^1$ and $R^2$ each independently represent a hydrocarbon group, a halogen atom, a hydroxyl group, an alkoxy group, a carboxyl group, an aryloxy group, an aralkyloxy group, an alkoxycarbonyl group, an aryloxycarbonyl group, an aralkyloxycarbonyl group, or an amino group optionally substituted with a hydrocarbon group; and n and m each independently represent an integer of 0 to 4, which mothod comprises reacting a metal hydride with an anthraquinone of (I):

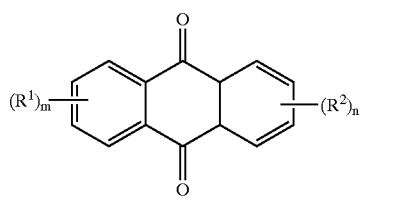

(I)

wherein $R^1$, $R^2$, m and n represent the same as defined above, and reacting the resulting reaction mixture with a primary alcohol.

DETAILED DESCRIPTION OF THE INVENTION $R^1$ and $R^2$ of formula (I) and (II) will be explained first.

Examples of the hydrocarbon group represented by $R^1$ or $R^2$ include a hydrocarbon group having approximately C1–C8 carbon atoms.

Examples of the hydrocarbon group include:
an alkyl such as methyl, ethyl, isopropyl, n-butyl, t-butyl, n-penthyl, n-hexyl, n-heptyl, and n-octyl groups;
an aryl group such as phenyl group; and
an aralkyl group such as a benzyl group, a phenethyl group.

Examples of the halogen atom include fluorine, chloride, bromine, and iodine.

The alkoxy, aryloxy, aralkyloxy, alkoxycarbonyl, aryloxylcarbonyl, and aralkyloxycarbonyl groups represented by $R^1$ or $R^2$ include those groups that are comprised of the alkyl, aryl and aralkyl groups as defined above, and an oxy or oxycarbonyl group respectively.

Examples of the alkoxy group include, for example, methoxy, ethoxy, isopropoxy, n-butoxy, t-butoxy, n-penthyloxy, n-hexyloxy, n-heptyloxy and n-octyloxy groups.

Examples of the aryloxy group include phenoxy group.

Examples of the aralkyloxy group include, for example, benzyloxy and phenethyloxy groups.

Examples of the alkoxycarbonyl group include methoxycarbonyl, ethoxycarbonyl, isopropoxycarbonyl, n-butoxycarbonyl, t-butoxycarbonyl, n-penthyloxycarbonyl, n-hexyloxycarbonyl, n-heptyloxycarbonyl and n-octyloxycarbonyl groups.

Examples of the aryloxylcarbonyl group include, for example, a phenoxycarbonyl group.

Examples of the aralkyloxycarbonyl group include benzyloxycarbonyl and phenethyloxycarbonyl groups.

Examples of the amino group include an amino group optionally substituted with a hydrocarbon group as defined above for the hydrocarbon group represented by $R^1$ and $R^2$. Specific examples thereof include methyl-, ethyl-, phenyl-, or dimethyl-amino group. Anthraquinones (I) also includes an anthraquinone of formula (I) wherein $R^1$ and/or $R^2$ represent a hydroxy or carboxyl (COOH) group which is forming a salt with lithium, potassium, or sodium.

The hydrocarbon group is preferred as $R^1$ and $R^2$, and the alkyl group is more preferred.

Examples of the anthraquinone of formula (I) include anthraquinone, 1-methylanthraquinone, 2-t-butylanthraquinone, 2,5-dimethylanthraquinone, 2-phenylanthraquinone, 2,6-dibenzylanthraquinone, 1-chloroanthraquinone, 2-bromo-6-chlororanthraquinone, 1-hydroxyanthraquinone, 2,3-dimethoxyanthraquinone, 2-methylaminoanthraquinone, 2,3-dicarboxyanthraquinone, 1,8-dimethoxycarbonylanthraquinone, and 1,8-diphenoxycarbonylanthraquinone.

Examples of the metal hydride include, for example, an alkali metal borohydride compound such as lithium borohydride and sodium borohydride. Preferred are alkali metal borohydride. The metal hydride is usually used in an amount of at least 0.5 mole, preferably, at least 2 moles per mol of the anthraquinone of formula (I) and from an economical viewpoint, 10 moles or less is preferable.

The anthraquinone of formula (I) is usually reacted with the metal hydride in an organic solvent.

Examples of the organic solvent include a secondary alcohols such as isopropanol and 2-butanol; a tertiary alcohol such as t-butanol; an aprotic polar solvent such as N,N-dimethylformamide or dimethylsulfoxide; an ether solvent such as di-isopropyl ether, diethylene glycol dimethyl ether, 1,4-dioxane, or tetrahydrofurane; a halogenated hydrocarbon solvent such as dichloromethane, dichloroethane, or chlorobenzene; an aromatic hydrocarbon such as benzene, toluene, or xylene; an aliphatic hydrocarbons such as hexane or heptane; and a mixture thereof. The organic solvent is usually used in an amount of at least about 1 part by mass but not more than about 50 parts by mass, preferably, at least about 5 parts by mass but not more than about 20 parts by weight to 1 part by mass of the anthraquinone of formula (I). Among these organic solvents, the alcohols are preferably used and more preferred are the secondary alcohol.

The anthraquinone of formula (I) is reacted with the metal hydride usually by mixing them in an organic solvent under an inert gas atmosphere such as nitrogen. The anthraquinone (I) and the metal hydride may be reacted in such a manner that they are completely dissolved in the organic solvent or are allowed to be partially dissolved in the solvent, which means that they are present partially in a solid form without being completely dissolved in the solvent.

The reaction of the present invention is usually conducted at 0° C. or higher, preferably, 50° C. or higher but not higher than 120° C. When the boiling point of organic solvent is less than 120° C., the reaction temperature is preferably set at a temperature below the boiling point. The reaction time is usually at least about 0.5 hour but not longer than about 12 hours.

As described above, the reaction mixture comprising the anthraquinones (I) with the metal hydride is obtained by mixing them, and it is then reacted with a primary alcohol by mixing the mixture and the primary alcohol in the present invention.

Examples of the primary alcohol include, for example, methanol, ethanol, 1-propanol, and 1-butanol, which can be used alone or as a combination of two or more of them. The primary alcohol is usually used in an amount of at least 0.1 part by mass, preferably, at least 0.5 part by mass but usually not higher than 5 parts by mass per 1 part by mass of the anthraquinone (I).

The mixing of the primary alcohol and the reaction mixture resulting in the step (a) is conducted, for example, by dropwise addition of the primary alcohol.

The reaction mixture is usually mixed with the primary alcohol at a temperature of 0° C. or higher, preferably, 50° C. or higher but usually not higher than 120° C. However, in the case where the boiling point of the primary alcohol or the organic solvent used in the previous reaction step is lower than 120° C., then the mixing temperature is usually set at a temperature lower than the boiling point.

The reaction is usually conducted over a period of not less than 0.2 hour but not longer than 7 hours, preferably not less than 0.3 hour but not longer than 5 hours.

After reaction by mixing was completed, the resulting reaction mixture may be kept at a temperature of 0° C. or higher, preferably 50° C. or higher and not exceeding 120° C. In the case where the boiling point of either the primary alcohol or solvent(s) used in previous reaction step is below 120° C., then the temperature is set at a temperature below the boiling point. The reaction mixture is usually kept at the temperature over a period of not longer than 5 hours.

The reaction mixture after mixing with the primary alcohol(s) is preferably further mixed with an acid. By mixing with the acid the yield of anthracene (II) can be improved. Examples of the acid include, for example, an organic acid including a carboxylic acid such as formic acid, acetic acid, butyric acid, valeric acid, oxalic acid, glycolic acid, or benzoic acid; and an inorganic acid such as hydrochloric acid, sulfuric acid, or phosphoric acid. The acid is usually used in such an amount that allows the pH of the reaction mixture 7 or lower, and it is typically 2 moles, preferably, 20 moles but usually not more than 100 moles per mol of the anthraquinone (I), and the amount may vary depending on the amount of the alkali metal hydride used in the previous step.

The acid is mixed with the reaction mixture usually at 0° C. or higher, preferably, 50° C. or higher but usually not higher than 120° C. However, in the case where the boiling point of the organic solvent or the primary alcohol used in the previous reaction is lower than 120° C., the temperature not higher than the boiling point is preferably. The reaction is carried out by mixing the reaction mixture with an appropriate acid over a reaction time of usually at least 0.2 hour but not longer than seven hours, preferably, at least 0.3 hour but not longer than 5 hours. After mixing is completed, the reaction mixtures may be kept at a temperature of usually 0° C. or higher, preferably, 50° C. or higher but usually not higher than 120° C. However, in the case where the boiling point of the primary alcohol or the organic solvent used in the previous reaction step is less than 120° C., the reaction mixture is preferably kept at a temperature of not higher than the boiling point for a period of usually from five hours or shorter.

The anthracene (II) can be collected from either the reaction mixture obtained by mixing the above reaction mixture with a primary alcohol or that obtained by further mixing the same with an acid. To collect the anthracene (II), for instance, the reaction mixture may be mixed with an insufficient solvent such as water to precipitate the anthracene (II) and the desired copound can be collected as crystals. In order to mix the reaction mixture with the insufficient solvent the latter may be added to the former or vice versa. The precipitated crystals can be readily collected by a method such as filtration.

After distilling the organic solvent or the primary alcohol out of the reaction mixture to obtain a residue, the anthracene (II) may be extracted from the residue with a suitable solvent. After removal of the solvent the anthracene (II) can be obtained in a crystalline form and collected anthracene (II) may be further purified by a method such as recrystallization, if necessary.

Examples of the anthracenes (II) thus obtained include, for example, anthracene, 1-methylanthracene, 2-t-butylanthracene, 2,5-dimethylanthracene, 2-phenylanthracene, 2,6-dibenzylanthracene, 1-chloroanthracene, 2-bromo-6-chlororanthracene, 1-hydroxyanthracene, 2,3-dimethoxyanthracene, 2-methylaminoanthracene, 2,3-dicarboxyanthracene, 1,8-dimethoxycarbonylanthracene, and 1,8-diphenoxycarbonylanthracene.

EXAMPLE

The present invention will be explained with reference to the preferred embodiments according to the present invention but should not be limited thereto.

Example 1

Under nitrogen atmosphere 13.22 g (50 mmol) of 2-tert-butylanthraquinone, 5.30 g (140.1 mmol) of sodium borohydride and 132.16 g of isopropyl alcohol were mixed and heated to 82° C., and stirred for 3 hours at the same temperature under reflux to obtain a reaction mixture. Quantitative analysis by gas chromatography indicated that 6.12 g of 2-tert-butylanthracene was contained in the reaction mixture, and the amount corresponded to 51.2% yield based on the amount of 2-tert-butylamthraquinone used as the starting material.

Thereafter, to the reaction mixture thus obtained 14.8 g of ethanol was added dropwise under stirring at a temperature ranging from 75° C. to 85° C. over 30 min. After completion of dropwise addition, the resulting mixture was further stirred for 2 hours at the same temperature range as above. Quantitative analysis by gas chromatography indicated that the reaction mixture contained 9.00 g of 2-tert-butylanthracene, and the amount corresponded to 76.8% yield, based on the amount of 2-tert-butylamthraquinone used as the starting material.

Then to the reaction mixture thus obtained, 26.43 g of acetic acid was added dropwise under stirring at a temperature range of from 75° C. to 85° C. over 30 min. After completion of dropwise addition, the resulting mixture was further stirred for 1 hour at the same temperature range as above.

Quantitative analysis by gas chromatography indicated that the reaction mixture contained 10.67 g of 2-tert-butylanthracene, and the amount corresponded to 91.1% yield, based on the amount of 2-tert-butylamthraquinone used as the starting material.

Example 2

Under nitrogen atmosphere 108.37 g (410 mmol) of 2-tert-butylanthraquinone, 43.43 g (1.148 mol) of sodium borohydride and 1,083.7 g of isopropyl alcohol were mixed and heated to 82° C., and stirred for 3 hours at the same temperature under reflux to obtain a reaction mixture. Quantitative analysis by gas chromatography indicated that the reaction mixture contained 48.65 g of 2-tert-butylanthracene, and the amount corresponded to 50.5% yield, based on the amount of 2-tert-butylamthraquinone used as the starting material.

Thereafter, to the reaction mixture thus obtained 121.38 g of ethanol was added dropwise under stirring at a temperatures range of from 75° C. to 85° C. over 30 min. After completion of dropwise addition, the resulting mixture was further stirred for 2 hours at the same temperature range as above.

Quantitative analysis by gas chromatography indicated that the reaction mixture contained 73.21 g of 2-tert-butylanthracene, and the amount corresponded to 76.0% yield, based on the amount of 2-tert-butylamthraquinone used as the starting material.

Then to the reaction mixture thus obtained 216.74 g of acetic acid was added dropwise under stirring at a temperature range of from 75° C. to 85° C. over 30 min. After completion of dropwise addition, the resulting mixture was further stirred for another 1 hour at the same temperature range as above. Quantitative analysis by gas chromatography indicated that the reaction mixture contained 86.9 g of 2-tert-butylanthracene, and the amount corresponded to 90.2% yield, based on the amount of 2-tert-butylamthraquinone used as the starting material.

To 866 g of water warmed at 30° C. in an nitrogen atmosphere, 1552. 5 g of the above obtained reaction mixture was added under stirring under over 30 minutes. The temperature of the reaction mixture was raised to 60° C. while stirring followed by successive stirring for 1 hour at the same temperature, and then cooled down to 0° C. over 6 hours to precipitate crystals. The precipitated crystals were collected by filtration, washed twice with 217 g of isopropyl alcohol, and dried in vacuo at 60° C. to obtain 64.7 g of 2-tert-butylanthracene in a white crystalline form (purity 99% or more). It was revealed by gas chromatography analysis that the filtrate contained 22 g of 2-tert-butylanthracene.

As described above, the method according to the present invention provides the anthracene (II) in a good yield.

While what are at present considered to be the preferred embodiments of the invention have been described, it will be understood that various modifications may be made therein, and the appended claims are intended to cover all such modifications as fall within the true spirits and scope of the invention.

What is claimed is:

1. A method for producing an anthracene of formula (II):

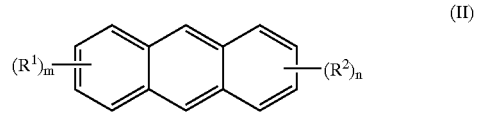

(II)

wherein $R^1$ and $R^2$ each independently represent a hydrocarbon group, a halogen atom, a hydroxyl group, an alkoxy group, a carboxyl group, an aryloxy group, an aralkyloxy group, an alkoxycarbonyl group, an aryloxycarbonyl group, an aralkyloxycarbonyl group, or an amino group optionally substituted with a hydrocarbon group; and n and m each independently represent an integer of 0 to 4, which method comprises the steps of:

(a) reacting a metal hydride with an anthraquinone of (I):

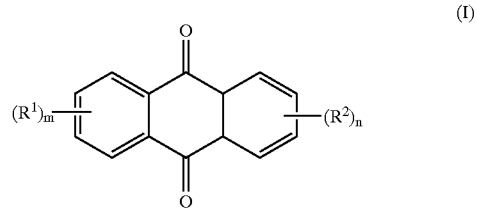

(I)

wherein $R^1$, $R^2$, m and n represent the same as defined above, and (b) reacting the resulting reaction mixture in step (a) with a primary alcohol.

2. A method according to claim 1, wherein said reaction mixture in step (a) is a reaction mixture obtained by reacting said metal hydride with said anthraquinone of formula (I) in an organic solvent.

3. A method according to claim 2, wherein said organic solvent is a secondary alcohol.

4. A method according to claim 1, wherein said primary alcohol is used in an amount of at least 0.1 part by mass but not higher than 5 parts by mass per 1 part by mass of said anthraquinone of formula (II).

5. A method according to claim 1, wherein said reaction mixture is reacted with said primary alcohol at a temperature range of from 50° C. to 120° C.

6. A method according to claim 1, wherein said reaction mixture is mixed with said primary alcohol for at least 0.2 hour but not longer than seven hours.

7. A method according to claim 1, wherein said reaction mixture and said primary alcohol are mixed and then mixed with an acid.

8. A method according to claim 7, wherein said acid is mixed at a temperature range of from 50° C. to 120° C.

9. A method according to claim 1, wherein the organic solvent is an organic solvent selected from a secondary alcohol, a tertiary alcohol, an aprotic polar solvent, an ether, a halogenated hydrocarbon, an aromatic hydrocarbon, aliphatic hydrocarbon, or a mixture thereof.

* * * * *